US009480255B2

(12) United States Patent
Piaggesi et al.

(10) Patent No.: US 9,480,255 B2
(45) Date of Patent: Nov. 1, 2016

(54) AGRICULTURAL COMPOSITION, METHOD FOR THE PRODUCTION THEREOF AND USES IN THE TREATMENT OF CULTURES

(75) Inventors: Alberto Piaggesi, Lanciano (IT); Gianluca Di Tommaso, San Vito Chietino (IT); Donata Di Tommaso, Mozzagrogna (IT)

(73) Assignee: Valagro S.P.A., Piazzano di Atessa (Chieti) (IT)

( * ) Notice: Subject to any disclaimer, the term of this patent is extended or adjusted under 35 U.S.C. 154(b) by 1442 days.

(21) Appl. No.: 13/056,327

(22) PCT Filed: Aug. 3, 2009

(86) PCT No.: PCT/IB2009/006451
§ 371 (c)(1),
(2), (4) Date: Mar. 15, 2011

(87) PCT Pub. No.: WO2010/015913
PCT Pub. Date: Feb. 11, 2010

(65) Prior Publication Data
US 2011/0160060 A1 Jun. 30, 2011

(30) Foreign Application Priority Data
Aug. 4, 2008 (IT) .............................. MI2008A1458

(51) Int. Cl.
*A01N 55/02* (2006.01)
*A01N 43/16* (2006.01)

(52) U.S. Cl.
CPC ..................................... *A01N 43/16* (2013.01)

(58) Field of Classification Search
None
See application file for complete search history.

(56) References Cited

U.S. PATENT DOCUMENTS 3,961,932 A * 6/1976 Miller ................................. 71/1
4,048,324 A 9/1977 Kohn
5,962,717 A 10/1999 Nonomura et al.
5,965,545 A * 10/1999 Ben-Shalom et al. .......... 514/55
5,993,504 A 11/1999 Nonomura et al.
6,407,040 B1 6/2002 Nichols
6,589,942 B1 7/2003 Ben-Shalom et al.
6,849,576 B2 * 2/2005 Suzuki et al. ............. 504/116.1

FOREIGN PATENT DOCUMENTS

| WO | WO 89/07395 A1 * | 8/1989 | ............. A01N 43/16 |
| WO | 9709879 A | 3/1997 | |
| WO | 9926898 A | 6/1999 | |
| WO | 0032041 A | 6/2000 | |
| WO | 0119187 A | 3/2001 | |
| WO | WO 01/19187 A1 * | 3/2001 | ............. A01N 43/16 |
| WO | 02069705 A1 | 9/2002 | |

OTHER PUBLICATIONS

Wu, et al, "Role of PH in Metal Adsorption From Aqueous Solutions Containing Chelating Agents on Chitosan", Ind. Eng. Chem. Res., vol. 38, 1999, pp. 270-275, XP002531031.
Colby, "Calculating Synergistic and Antagonistic Responses of Herbicide Combinations", Weeds, Weed Society of America, Urbana, IL, United States, vol. 15, Jan. 1, 1967, pp. 20-22, XP001112961.

* cited by examiner

*Primary Examiner* — Alton Pryor
(74) *Attorney, Agent, or Firm* — Meunier Carlin & Curfman LLC

(57) ABSTRACT

The present invention relates to an agricultural composition and the uses thereof to protect crops against attack by plant pathogens and/or to improve the resistance of crops to infections caused by said pathogenic agents and/or to enhance the tolerance thereof to abiotic stresses, such as those caused by cold, salinity and drought. Said composition comprises an association of an at least partially depolymerized chitosan with a bivalent copper chelate. The composition has shown to be particularly suitable-for treating oidium infections. It is moreover useful against the propagation of viruses and/or particularly effective as a biostimulant to plant and fruit growth and/or able to extend the shelf life of fruit and seeds.

31 Claims, 2 Drawing Sheets

AGRICULTURAL COMPOSITION, METHOD FOR THE PRODUCTION THEREOF AND USES IN THE TREATMENT OF CULTURES

The present invention relates to an agricultural composition, a method for the preparation thereof and the uses thereof to protect crops against attack by plant pathogens, including viruses, and/or to improve the resistance of crops to infections caused by said pathogenic agents and/or to enhance the tolerance thereof to abiotic stresses, such as those caused by cold, salinity and drought.

Said composition has also shown to be particularly useful against the propagation of viruses and/or particularly effective as a biostimulant conducive to plant and fruit growth and/or able to extend the shelf life of fruit and seeds.

The composition of the present invention comprises a suitable synergetic association of active ingredients, preferably in a mixture with suitable excipients and/or solvents and/or vehicles, which are capable of exerting their action directly on phytopathogenic agents or of stimulating the natural endogenous resistance of plants by activating a series of signal transduction pathways within the plant itself. This serves to optimise the potential response of the plant organism, correlated with its resistance to infection and/or to abiotic stress.

The known techniques for controlling phytopathogens generally consist in treating plants with pesticides which have a direct toxic activity on the invading pathogen or on the pathogen carrier. Consequently, agriculture and horticulture strongly depend on regular applications (e.g. by spraying) of fungicides, to control fungal diseases, and of insecticides and/or nematocides, to control the carriers of viral diseases.

Another approach for controlling phytopathogens consists in seeking to stimulate the plant's natural resistance so as to prevent the action of the pathogens and/or significantly limit the aggressiveness thereof.

However, a series of problems have been encountered with the agricultural formulations developed in the sector to stimulate plant resistance as a practical disease control procedure. Said problems have included, for example, phytotoxicity (yellowing, necrosis and general plant diseases), a frequent lack of truly significant levels of disease control and non-reproducibility/non-sustainability.

There is thus a pressing need to have simple, effective products, devoid of undesirable side effects, which are able to stimulate, in an optimal manner, crop resistance to the largest possible number of phytopathogens (irrespective of their origin) and to the abiotic stresses mentioned above.

The aim of the present invention is to provide a suitable answer for the above-described problems.

Accordingly, one object of the present invention is to provide an agricultural composition for improving plant resistance to diseases, while avoiding the disadvantages of the prior art; precisely, it is an object of the present invention to provide robust, broad-spectrum protection, preferably of a preventive type, against plant pathogens which avoids the occurrence of disadvantageous side effects.

Another object of the present invention is to provide an agricultural composition that is able increase plant tolerance to abiotic stress, for example against such factors as cold, salinity and drought.

Chitosan is a well-known derivative of chitin, obtainable by partial or total N-deacetylation of the latter. Structurally, chitosan is a copolymer of D-glucosamine and N-acetyl-D-glucosamine, linked by β-1,4-glycosid bonds, having an average molecular weight greater than 1 mDa and corresponding to a chain of approximately 5000 monomer units. Many different applications of chitosan are known. For example, it is used in waste treatment, in the paper industry, in medical and cosmetic products, in biotechnologies, in the foodstuff and feedstuff sector, and in membrane applications. In agriculture it has a potential use as: a coating, to coat seeds, leaves, fruit and vegetables; as a fertiliser, to stimulate and enhance plant growth; as a stimulant, to improve plant immunity and protection against harmful microorganisms.

However, as is well known, chitosan is insoluble in water (which represents the vehicle of choice in formulations intended for agricultural use) and in a diluted acid environment it forms highly viscous solutions, making delivery through the nozzles of common sprayers difficult/problematic. As such, therefore, it does not represent a satisfactory solution for the previously described problems.

Attempts to remedy the aforesaid disadvantages have led to the development of complex and costly formulations comprising chitosan and a number of other active or complementary components. However, the efficacy of said formulations is frequently inadequate for an optimal application in agriculture and horticulture.

Other attempts to remedy the above-mentioned disadvantages have sought to exploit the fact that a number of oligomers obtained by depolymerisation (chemical or enzymatic) of chitosan have revealed to be more water soluble than non-depolymerised chitosan and have moreover shown to possess a similar activity.

Further attempts have involved complexing chitosan or the oligomers thereof with metal ions (e.g. copper, zinc and aluminum), preferably so as to give chitosan/oligomer-metal chelate complexes.

However, these derivatives, too, have failed to provide the desired optimal answer for the above-described problems, for example because the water solubility of said metal chelates is not always complete.

The Applicant has now surprisingly found that an aqueous agricultural composition comprising at least partially depolymerised chitosan in association with other specific suitable components is able provide robust broad-spectrum protection against bacterial, fungal and viral phytopathogens without causing disadvantageous side effects, thus giving the desired answer for the problems illustrated previously.

Therefore, an object of the present invention concerns the above-mentioned aqueous composition, comprising a synergetic association of an at least partially depolymerised chitosan with a bivalent copper chelate, as set forth in the appended independent claim.

Another object of the invention concerns the use of said composition in agriculture to enhance crop resistance, preventive and non-preventive, to phytopathogenic agents and to abiotic stresses, as set forth in the appended independent claim.

A further object of the present invention concerns a method for preparing the above-mentioned composition, as set forth in the appended independent claim.

Preferred embodiments of the present invention are described in the appended dependent claims.

Figure 1:
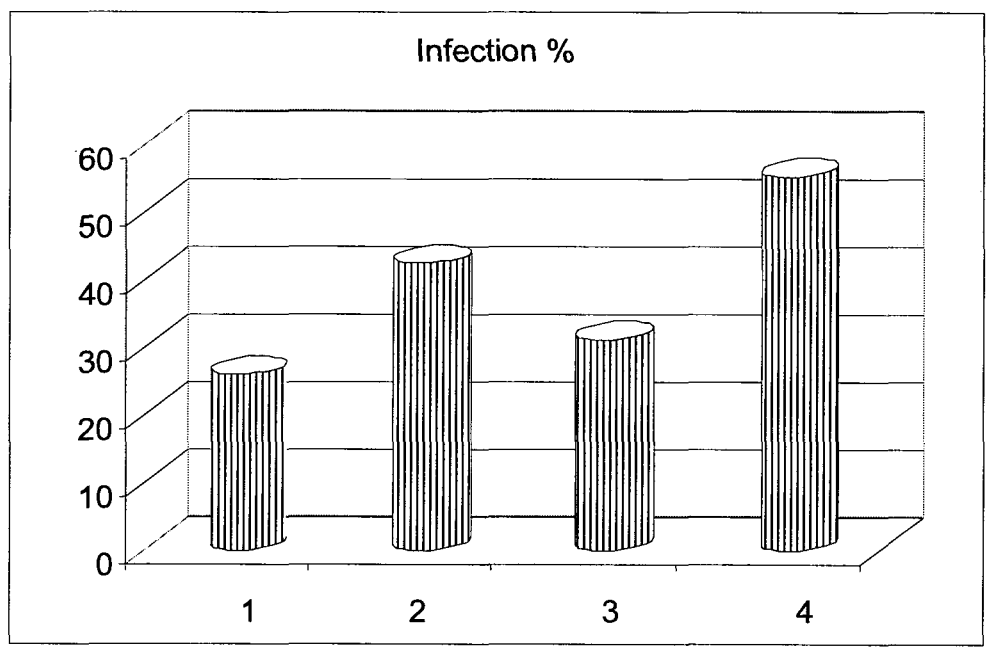
FIG. 1 depicts the effectiveness of certain compositions for controlling infection caused by odium on courgette plant leaves.

As disclosed above, the aqueous-based agricultural composition according to the present invention comprises a synergetic association of at least partially depolymerised chitosan with a bivalent copper chelate complex.

Preferably, the chitosan has a degree of acetylation (DA) comprised from 1% to 65%; more preferably, from 2% to 55%; most preferably, from 5% to 45%, with respect to the weight of completely deacylated chitosan. Preferably, the chitosan has a degree of depolymerisation of at least 10% by weight, with respect to the weight of non-depolymerised chitosan; more preferably, from about 12% to about 90%; most preferably, from about 15% to about 70%.

Preferably, the at least partially depolymerised chitosan has an inherent viscosity, measured at 30° C., of from 0.02 to 0.15 dL/g, more preferably from 0.03 to 0.11 dL/g, most preferably from 0.04 to 0.08 dL/g, (measured in a sample of 20 g in an amount of water such as to obtain a final volume of 100 ml, using a Cannon-Fenske Rov. 75 viscosimeter).

Preferably, the at least partially depolymerised chitosan has an average molecular weight of from about 1,000 to about 10,000.

In the composition of the present invention the at least partially depolymerised chitosan is present in a percentage amount of from about 0.5% to about 20% by weight, with respect to the total weight of the composition; preferably, from about 3% to about 12%.

Preferably, the bivalent copper chelate is selected from chelate complexes of $Cu^{2+}$ with suitable organic acid or amino acid chelants. Said chelants are suitably selected from those that assure complete solubility and stability in the solvent(s) used to prepare the composition.

The chelate complex of $Cu^{2+}$ with ethylenediamine tetraacetic acid (CuEDTA) has shown to be particularly preferable for the purposes of the present invention, whereas the use of other bivalent copper salts (such as copper sulphate, $CuSO_4$) has revealed to be particularly disadvantageous, because it renders the final formulation viscous and unusable. In contrast, the chelate complex CuEDTA gives rise to clear formulations thanks to its high degree of solubility in the formulation and its stability, which seems able to hamper or inhibit the formation of chitosan-copper chelate complexes.

In the composition of the present invention the chelate complex CuEDTA is present in a percentage amount ranging from about 0.05% to about 20% by weight, with respect to the total weight of the composition; preferably, from about 2% to about 15%.

Preferably, the composition according to the present invention may further comprise suitable adjuvants, additives and excipients which may improve its functional and applicative capabilities.

It is highly preferable, in particular, that the composition further comprises an effective quantity of at least one organic acid which is able to assure a complete solubility of the chitosan admixed with the depolymerisation products thereof.

Said at least one organic acid is preferably selected from water-soluble organic acids $C_1$-$C_{15}$.

Among them, preferred are those selected from: formic acid, acetic acid, propionic acid, butyric acid, ascorbic acid, citric acid, salicylic acid, acetylsalicylic acid and buffered solutions thereof (e.g. acetic acid 0.3M/sodium acetate 0.2M).

Acetic acid has shown to be particularly preferred. In a particularly preferred embodiment of the invention, 80% acetic acid is used.

In the composition of the present invention, said organic acid is present in an amount, expressed as weight percentage, of from about 1% to about 40%, preferably from about 5% to about 15%, with respect to the total weight of the composition.

For the purpose of preparing the composition according to the present invention it is possible to use a previously at least partially depolymerised chitosan.

For example, in one embodiment of the invention, the chitosan is previously depolymerised by a preferably partial hydrolysis, using chemical or enzymatic methods that are well known and commonly employed by those skilled in the art. The product resulting from said hydrolysis may be used as such, or after being purified.

More preferably, for the purpose of preparing the composition according to the present invention, it is also possible to use a native, i.e. non-depolymerised chitosan, and allow the at least partial depolymerisation reaction to occur spontaneously in situ, that is to say within the composition itself, at the end of the preparation thereof. Therefore, according to said preferred embodiment, in the composition of the present invention the at least partially depolymerised chitosan is obtained in situ by depolymerisation of native chitosan in the presence of at least one proteolytic enzyme.

In this case, together with the non-polymerised chitosan, an effective quantity of at least one proteolytic enzyme is added, which, in the acidic environment of the composition, achieves the desired at least partial depolymerisation of the chitosan.

Said proteolytic enzyme is preferably selected from: papain, pepsin, trypsin, bromelain, amylase, chitinase, chitosanase, glucosanase, lipase, tannase and protease. Preferably, said enzyme is selected from: papain, pepsin, trypsin, bromelain, amylase, and chitosanase.

The enzyme papain has shown to be particularly preferable. In this particularly preferred embodiment of the invention the initial amount of chitosan is substantially equal or analogous to those described previously, whereas said proteolytic enzyme is present in a percentage amount of from about 0.01% to about 2% by weight, with respect to the total weight of composition; preferably, from about 0.05% to about 0.3%.

The degree of depolymerisation obtained, within the previously specified limits, depends on the amount of enzyme added to the composition.

Preferably, after it has been prepared the composition is additionally subjected to a suitable heat treatment which, by deactivating the enzyme, assures and stabilises the desired degree of chitosan depolymerisation. Preferably, the heat treatment is started around 1-24 h, preferably 16-24 h, after completion of the formulation. Said heat treatment is performed at a temperature of from about 95° C. to about 110° C., preferably at about 105° C., for a period of time preferably from 10 min to 1 h. The preparation thus obtained is returned to room temperature (between around 20° C. and around 30° C., preferably at a temperature of around 25° C.) in a time of less than 1 h.

In another preferred embodiment, the composition according to the present invention may further comprise one or more compounds having a complementary action with respect to the chelate complex CuEDTA.

Said optional compounds are preferably selected from: chelate complexes of bivalent manganese with organic acid or amino acid chelants, such as the chelate complex of $Mn^{2+}$ with ethylenediamine tetraacetic acid (MnEDTA).

Moreover, said compounds can be selected from chelate complexes and/or salts of microelements, such as Boron (boric acid, sodium octoborate, boro-ethanol amine), Manganese ($Mn^{2+}$), Zinc ($Zn^{2+}$) and Iron ($Fe^{3+}$).

Preferably, the chelate complex MnEDTA is present in the composition of the invention in a percentage amount of from about 0.05% to about 15% by weight, with respect to the total weight of the composition; more preferably, in an amount of from about 1% to about 7%.

Overall, the salts of microelements can be present in a percentage amount of from about 0.05% to about 5.0%, with respect to the total weight of the composition; more preferably, in an amount of about 4%.

Preferably, the composition of the present invention may further comprise surfactants, i.e. substances that help to distribute the solution over the leaves during application by reducing the surface tension of water and enabling uniform and complete wetting.

Among said surfactants, particularly preferred are natural fatty alcohols $C_8$-$C_{10}$, such as alkylpolyglucosides.

Said surfactants are preferably present in a percentage amount of from about 0.1% to about 10% by weight, with respect to the total weight of the composition; more preferably, in an amount ranging from about 0.5% to about 3%.

In the composition of the present invention, water is present in an amount complementary to 100%, with respect to the total weight of the composition.

Preferably, the composition according to the present invention has a pH of from 3.5 to 5.0, more preferably from 4.0 to 4.5.

Merely by way of example, which in no way limits the scope of the invention, an illustration is given below of some of the possible preferred compositions of the present invention, with an indication of the weight percentage ranges of the components.

EXAMPLE 1

| | |
|---|---|
| Water | 10%-90% |
| Acetic acid 80% | 1%-40% |
| Chitosan (partially depolymerised) | 0.5%-20% |
| CuEDTA | 0.05%-20% |
| Alkylpolyglucosides | 0.1%-10% |

EXAMPLE 2

| | |
|---|---|
| Water | 10%-90% |
| Acetic acid 80% | 1%-40% |
| Chitosan (non-depolymerised) | 0.5%-20% |
| Papain | 0.01%-2% |
| CuEDTA | 0.05%-20% |
| MnEDTA | 0.05%-15% |
| Alkylpolyglucosides | 0.1%-10% |

EXAMPLE 3

| | |
|---|---|
| Water | 60%-80% |
| Acetic acid 80% | 5%-15% |
| Chitosan (non-depolymerised) | 3%-12% |
| Papain | 0.05%-0.3% |
| CuEDTA | 2%-15% |
| MnEDTA | 1%-7% |
| Alkylpolyglucosides | 0.1%-10% |

EXAMPLE 4

One of the Particularly Preferred Compositions

| | |
|---|---|
| Water | 74.9% |
| Acetic acid 80% | 5% |
| Chitosan (non-depolymerised) | 5% |
| Papain | 0.1% |
| CuEDTA | 10% |
| MnEDTA | 4.0% |
| Alkylpolyglucosides | 1% |

The compositions of the present invention are prepared in the traditional manner by adding the ingredients (the order in which they are added is not a limiting factor) in a suitable mixing apparatus equipped with agitation means and, if required, heating and refrigeration means.

The mixture of components is maintained under agitation until a clear solution is obtained, which, after filtration as necessary, is sent off for packaging.

As previously disclosed, when the partial depolymerisation reaction of the chitosan takes place in situ, the step of mixing the components is preferably followed by a step in which the mixture obtained is left to react at room temperature, under further agitation, for a suitable period of time, ranging from 1 h to 24 h, afterwards the resulting solution is submitted to a heat treatment, as already previously described, in order to deactivate the enzyme and stabilise the degree of chitosan depolymerisation as obtained.

The composition according to the present invention has shown to be particularly stable; it does not give rise to any degradation of active components and substantially maintains its appearance as a clear solution over time. Optionally, said composition may also be dried and packaged and sold as a solid powder to be reconstituted with the necessary quantity of water at the time of crop treatment.

The composition according to the present invention is not phytotoxic and substantially does not cause any side effects, such as yellowing, stunting of development, necrosis or any other deleterious effect.

The composition has shown to be able to function against a wide range of plant diseases.

In particular, with regard to a particularly preferred embodiment, said composition has demonstrated to be considerably effective against the damage caused by oidium.

For example, experimental field tests have shown an excellent effectiveness of the composition in controlling the disease caused by oidium in melons, with results demonstrating statistically significant differences compared to untreated products.

Analogous results against oidium have been obtained in plot tests conducted on the grape variety Montepulciano d'Abruzzo. It was found that the treatment gave rise, among other things, to a significant increase in resveratrol (stilbenes), one of the compounds most responsible for triggering the defense responses of a plant following an attack by pathogens.

Test n. 1: Oidium Infection on Courgette Leaves.

Plot trials were performed to test the ability to control oidium (*Leveillula taurica*) on the courgette, as illustrated in the following. Table 1 and in the corresponding graph in the appended FIG. 1, which shows the percentage values of the infection caused by oidium on courgette plant leaves.

TABLE 1

Parameters of *oidium* infection on courgette leaves

| Test plot | % infection | Effectiveness |
|---|---|---|
| 1 | 26 | 52.90 |
| 2 | 42.4 | 23.19 |
| 3 | 31.2 | 43.48 |
| 4 | 55.2 | 0 |

Plot 1=treated with the composition of the invention (comprising the partially depolymerised chitosan/CuEDTA association) described in Example 4;

Plot 2=treated with the same composition of Example 4, but devoid of CuEDTA;

Plot 3=treated with the same composition of Example 4, but devoid of chitosan and papain;

Plot 4=untreated control plot.

In all trials each composition was used in a dose equivalent to 10 ml/l and applied in an amount of 1000 l/ha.

The infection was determined as the surface area affected by the pathogen, expressed as a percentage of the entire leaf surface area. The effectiveness of the treatment was determined using the Abbott formula:

$$\left(1 - \frac{\text{pathogen population in the test plot considered}}{\text{pathogen population in the control plot}}\right) \times 100$$

Test n. 2: Oidium Infection on Melon Leaves.

Figure 2:
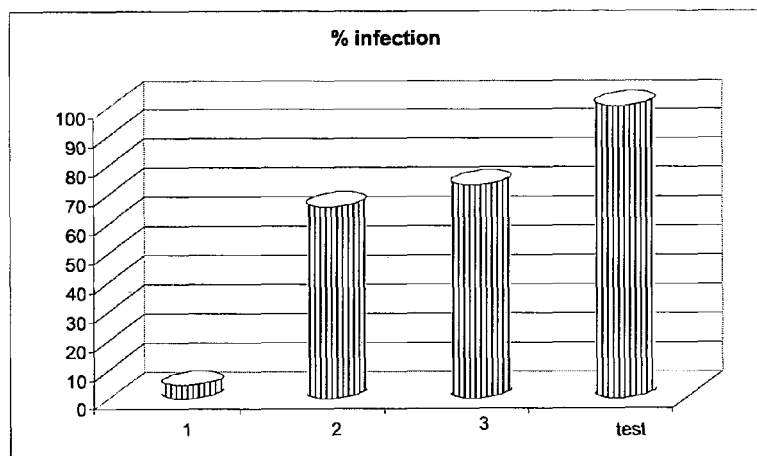
FIG. 2 depicts the effectiveness of certain compositions for controlling infection caused by odium on melon plant leaves.

Plot trials were performed to test the ability to control oidium (*Leveillula taurica*) on the melon, as illustrated in the following Table 2 and in the corresponding graph in the appended FIG. 2, which shows the percentage values of the infection caused by oidium on melon plant leaves.

TABLE 2

Parameters of *oidium* infection on melon leaves

| Test plot | % infection | Effectiveness |
|---|---|---|
| 1 | 4.5 | 95.5 |
| 2 | 65.6 | 35.6 |
| 3 | 73.2 | 26.8 |
| 4 | 100.0 | 0 |

Plot 1=treated with the composition of the invention (comprising the partially depolymerised chitosan/CuEDTA association) described in Example 4;

Plot 2=treated with the same composition of Example 4, but devoid of CuEDTA;

Plot 3=treated with the same composition of Example 4, but devoid of chitosan and papain;

Plot 4=untreated control plot.

In all trials each composition was used in a dose equivalent to 10 ml/l and applied in an amount of 1000 l/ha.

The percentage of infection and effectiveness were determined as described above for Test 1.

Test n. 3: Oidium Infection on Tomato Plant Leaves.

Figure 3:
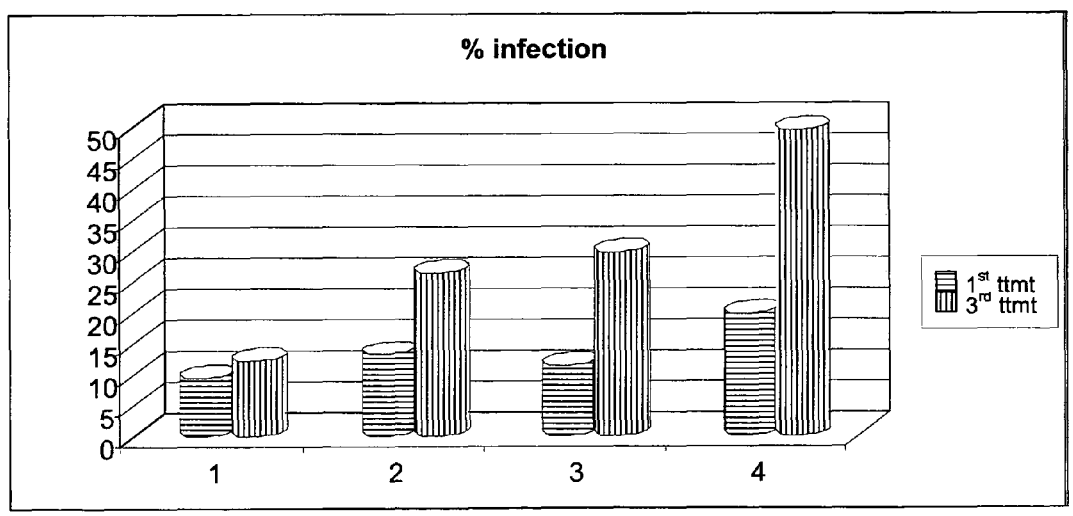
FIG. 3 depicts the effectiveness of certain compositions for controlling infection caused by odium on tomato plant leaves.

Plot trials were performed to test the ability to control oidium (*Leveillula taurica*) on the tomato, as illustrated in the following Tables 3 and 4 and in the corresponding graph in the appended FIG. 3, which shows the percentage values of the infection caused by oidium on tomato plant leaves, respectively 5 days after the first treatment and 5 days after the third (and last) treatment.

TABLE 3

Parameters of *oidium* infection on tomato leaves (5 days after the first application)

| Test plot | % infection | Effectiveness |
|---|---|---|
| 1 | 6.5 | 67.0 |
| 2 | 13.2 | 33.3 |
| 3 | 11.4 | 42.4 |
| 4 | 19.8 | 0 |

TABLE 4

Parameters of *oidium* infection on tomato leaves (5 days after the third application and 13 days after the second one)

| Test plot | % infection | Effectiveness |
|---|---|---|
| 1 | 12.3 | 75.3 |
| 2 | 26.3 | 47.0 |
| 3 | 29.8 | 39.9 |
| 4 | 49.5 | 0.00 |

Plot 1=treated with the composition of the invention (comprising the partially depolymerised chitosan/CuEDTA association) described in Example 4;

Plot 2=treated with the same composition of Example 4, but devoid of CuEDTA;

Plot 3=treated with the same composition of Example 4, but devoid of chitosan and papain;

Plot 4=untreated control plot.

In all trials each composition was used in a dose equivalent to 10 ml/l and applied in an amount of 1000 l/ha.

The percentage of infection and effectiveness were determined as described above for Test 1.

The percentage of infection caused by oidium was advantageously reduced, compared to the untreated control (plot 4), by the partially depolymerised chitosan/CuEDTA association (plot 1), and to a significantly greater extent than that achieved with analogous treatments using the two components applied individually (plots 2 and 3 respectively). The synergy of action between the two ingredients characterising the association of the agricultural composition of the present invention thus becomes apparent.

Said composition has also shown to be compatible with biocontrol agents such as benign bacteria and mushrooms. Furthermore, said composition has proven useful both for better disease control (preventive and non-preventive), and for improved plant nutrition and growth.

By way of example, the biostimulating activity of the composition of the present invention on the productive performance of tomatoes grown in hothouse was evaluated via comparison with an untreated control plot. With respect to this latter control plot, the composition of the present invention was able to achieve a significant increase in the average berry weight, of about 15% and even greater.

The agricultural composition according to the invention can be applied on plant leaves and roots by spraying, soaking, lengthy immersion, coating of seeds and using fertigation systems.

Furthermore, by applying the composition of the present invention on fruit, a significant improvement in the preservation and exterior appearance thereof during the storage period was achieved.

The present invention therefore refers to a stable, synergetic agricultural composition of simple constitution, preparation and application, which is particularly useful for obtaining an improvement in crop resistance to infection by phytopathogenic agents, including viruses, and/or for phytotherapeutically treating crops, and/or for increasing crop tolerance to abiotic stresses, e.g. against cold, salinity and drought. Said composition has also shown to be particularly useful as a fertiliser for stimulating plant and fruit growth and moreover for extending the shelf life of fruit and seeds. Finally, the present invention also concerns a method for improving the resistance of crops to infection by phytopathogenic agents, including viruses, and/or for phytotherapeutically treating crops, and/or for increasing crop tolerance to abiotic stresses and/or as a fertilizer for stimulating plant and fruit growth and/or extending the shelf life of fruit and seeds, comprising administering to said crops or said fruit or said seeds an effective amount of a composition of the invention as previously described.

The invention claimed is:

1. An aqueous agricultural composition comprising:
    a) an at least partially depolymerized chitosan;
    b) a bivalent copper chelate, wherein the chelate comprises an organic acid or amino acid; and
    c) a water soluble $C_1$-$C_{15}$ organic acid and wherein the chelate is completely soluble in the aqueous composition in an amount effective to completely solubilize the chitosan in the aqueous composition.

2. The composition according to claim 1, wherein said at least partially depolymerised chitosan has a degree of depolymerisation of at least 10% by weight, with respect to the weight of non-depolymerised chitosan.

3. The composition according to claim 1, wherein said at least partially depolymerised chitosan has an inherent viscosity, measured at 30° C., of from 0.02 to 0.15 dL/g.

4. The composition according to claim 3, wherein said at least partially depolymerised chitosan has an inherent viscosity, measured at 30° C., of from 0.03 to 0.11 dL/g.

5. The composition according to claim 4, wherein said at least partially depolymerised chitosan has an inherent viscosity, measured at 30° C., of from 0.04 to 0.08 dL/g.

6. The composition according to claim 1, wherein said at least partially depolymerised chitosan has an average molecular weight of from about 1,000 to about 10,000.

7. The composition according to claim 1, wherein said at least partially depolymerised chitosan is present in a percentage amount of from about 0.5% to about 20% by weight, with respect to the total weight of the composition.

8. The composition according to claim 7, wherein said at least partially depolymerised chitosan is present in a percentage amount of from about 3% to about 12% by weight, with respect to the total weight of the composition.

9. The composition according to claim 1, wherein the copper chelate comprises CuEDTA.

10. The composition according to claim 9, wherein CuEDTA is present in a percentage amount of from about 0.05% to about 20% by weight.

11. The composition according to claim 10, wherein CuEDTA is present in a percentage amount of from about 2% to about 15% by weight.

12. The composition according to claim 1, wherein the water soluble $C_1$-$C_{15}$ organic acid comprises formic acid, acetic acid, propionic acid, butyric acid, ascorbic acid, citric acid, salicylic acid or acetylsalicylic acid.

13. The composition of claim 12, wherein the water soluble $C_1$-$C_{15}$ organic acid comprises acetic acid.

14. The composition according to claim 1, wherein the organic acid is present in a percentage amount of from about 1% to about 40% by weight, with respect to the total weight of the composition.

15. The composition according to claim 14, wherein the organic acid is present in a percentage amount of from about 5% to about 15% by weight, with respect to the total weight of the composition.

16. The composition according to claim 1, wherein said at least partially depolymerised chitosan is obtained in situ by depolymerisation of native chitosan in the presence of at least one proteolytic enzyme.

17. The composition according to claim 16, wherein said at least one proteolytic enzyme comprises papain, pepsin, trypsin, bromelain, amylase, chitinase, chitosanase, glucosanase, lipase, tannase or protease.

18. The composition according to claim 17, wherein said at least one proteolytic enzyme comprises papain.

19. The composition according to claim 16, wherein said at least one proteolytic enzyme is present in a percentage amount of from about 0.01% to about 2% by weight, with respect to the total weight of the composition.

20. The composition according to claim 19, wherein said at least one proteolytic enzyme is present in a percentage amount of from about 0.05% to about 0.3% by weight, with respect to the total weight of the composition.

21. The composition according to claim 1, further comprising a manganese chelate, wherein the chelate comprises an organic acid or amino acid.

22. The composition according to claim 21, wherein the manganese chelate comprises MnEDTA.

23. The composition according to claim 21, wherein the manganese chelate is present in a percentage amount of from about 0.05% to about 15% by weight, with respect to the total weight of the composition.

24. The composition according to claim 23, wherein the manganese chelate is present in a percentage amount of from about 1% to about 7% by weight, with respect to the total weight of the composition.

25. The composition according to claim 1, further comprising alkylpolyglucosides in a percentage amount of from about 0.1% to about 10%, with respect to the total weight of the composition.

26. The composition according to claim 1, further comprising alkylpolyglucosides in a percentage amount of from about 0.5% to about 3%, with respect to the total weight of the composition.

27. The composition according to claim 1, having a pH of from 3.5 to 5.0.

28. The composition according to claim 27, having a pH of from 4.0 to 4.5.

29. A method of improving crop, plant or fruit resistance to infection by phytopathogenic agents, comprising administering to the crop, plant or fruit an effective amount of the composition of claim 1.

30. A method of treating a crop, plant or fruit infected with oidium comprising administering to the infected crop, plant or fruit the composition of claim 1 in an amount effective to treat oidium.

31. A method of stimulating crop, plant or fruit growth, comprising administering to the crop, plant or fruit an effective amount of the composition of claim 1.

* * * * *